(12) United States Patent
Wolter et al.

(10) Patent No.: US 7,258,047 B1
(45) Date of Patent: Aug. 21, 2007

(54) ORTHODONTIC PLIERS AND METHODS OF USING THE SAME

(76) Inventors: Thomas J. Wolter, 8783 Three Chimmneys Dr., Germantown, TN (US) 38138; Steven A. Galella, 384 New Byhalia, Collierville, TN (US) 38017

( * ) Notice: Subject to any disclaimer, the term of this patent is extended or adjusted under 35 U.S.C. 154(b) by 279 days.

(21) Appl. No.: 10/950,878

(22) Filed: Sep. 27, 2004

(51) Int. Cl.
  *B25B 7/02* (2006.01)
  *B25B 7/04* (2006.01)
  *B25B 7/06* (2006.01)
  *A61C 3/00* (2006.01)

(52) U.S. Cl. ............................ 81/416; 81/415; 81/417; 81/427; 81/341; 433/4

(58) Field of Classification Search .......... 81/415–417, 81/427, 341; 433/4
See application file for complete search history.

(56) References Cited

U.S. PATENT DOCUMENTS

| | | | | |
|---|---|---|---|---|
| 2,385,835 | A | * 10/1945 | Neal | ............................ 30/250 |
| 2,806,394 | A | * 9/1957 | Briegel | ..................... 72/409.19 |
| 2,944,341 | A | 7/1960 | Lane | |
| 3,069,686 | A | 12/1962 | Smith | |
| 4,903,558 | A | * 2/1990 | le Duc | ......................... 81/416 |
| 5,065,650 | A | 11/1991 | Anderson | |
| 6,134,993 | A | * 10/2000 | Tally | ............................. 81/394 |
| 6,176,158 | B1 | * 1/2001 | Chen | ............................. 81/417 |
| 6,647,835 | B1 | 11/2003 | Tseng | |
| 2003/0152883 | A1 | 8/2003 | Smith | |
| 2005/0011321 | A1 | * 1/2005 | Hsien | ............................ 81/417 |

* cited by examiner

*Primary Examiner*—Joseph J. Hail, III
*Assistant Examiner*—Bryan R. Muller
(74) *Attorney, Agent, or Firm*—Wyatt, Tarrant & Combs, LLP

(57) ABSTRACT

The present invention relates to a pliers that includes first and second arms that are pivotally interconnected utilizing an appropriate mechanical fastener. A spring is generally disposed about the mechanical fastener to bias the pliers toward an open condition. Further, a bearing is generally located between the first and second arms to hinder friction between the first and second arms, facilitate movement of the pliers between open and closed conditions, and provide some control for the range of pivotal motion of the first arm relative to the second arm.

12 Claims, 3 Drawing Sheets

ORTHODONTIC PLIERS AND METHODS OF USING THE SAME

STATEMENT REGARDING RESEARCH/DEVELOPMENT FUNDING

Not applicable.

CROSS-REFERENCE TO RELATED APPLICATIONS

Not applicable.

BACKGROUND OF THE INVENTION

1. Field of the Invention

The invention generally relates to the fields of dentistry and orthodontics, and more particularly, to pliers to be utilized in dental and/or orthodontic procedures.

2. General Background of the Invention

Many types of pliers-type tools are utilized in orthodontic and dental procedures. Some pliers may be utilized to alter the shape, angle, and/or orientation of orthodontic wires. Other pliers may be utilized to for extracting teeth or other oral tissues. Still other pliers may be utilized for cutting oral tissue and/or dental wire.

To date, dental/orthodontic pliers have demonstrated a number of shortcomings. For instance, use of some pliers has resulted in undesired incidence of muscle fatigue in the hands and/or wrists of the user. This may be attributed to the repetitive motions of multiple wire bends or appliance adjustments associated with a number of orthodontic protocols. As another example, some pliers fail to enable a user to successfully provide desired bends, loops, torque, helices, and the like in dental wire. Another drawback of some orthodontic pliers is that they fail to demonstrate desired longevity and/or strength. In this regards, some pliers have been found to undesirably fail/deteriorate under normal usage including rigorous sterilization processes. Yet another drawback of some pliers is that they tend to be difficult to manipulate and/or utilize.

SUMMARY OF THE INVENTION

Accordingly, it is an object of the present invention to provide pliers that are ergonomically designed to reduce incidence of muscle fatigue. It is another object of the invention to provide pliers that are easy to utilize and enables a user to achieve desired results. Still another object of the invention is to provide pliers that are durable when exposed to normal usage and sterilization procedures. These benefits, as well as others, may be achieved by the present invention herein described.

The present invention is directed to pliers including first and second arms that are pivotally interconnected utilizing an appropriate mechanical fastener. A spring is generally disposed about the mechanical fastener to bias the pliers toward an open condition. Further, a bearing is generally located between the first and second arms to hinder friction between the first and second arms and facilitate movement of the pliers between open and closed conditions.

DETAILED DESCRIPTION OF THE PREFERRED EMBODIMENTS

Figure 1:
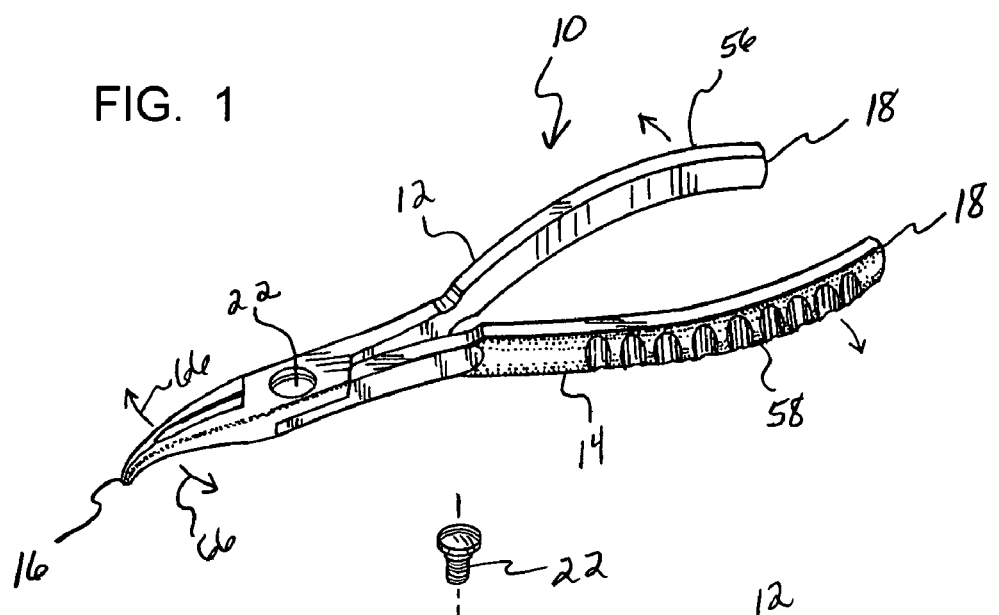
FIG. 1 is a perspective view of an orthodontic pliers of the invention in a closed condition.

The present invention will now be described in relation to the accompanying drawings, which at least assist in illustrating the various pertinent features thereof. While the preferred embodiment of the invention is shown and described as an orthodontic pliers, it should be noted that the invention may find application in any appropriate pliers assembly. FIG. 1 shows an orthodontic pliers 10 including a first arm 12 and a second arm 14. Each of these first and second arms 12, 14 defines a nose end 16 and an opposing handle end 18 of the orthodontic pliers 10. A length of the orthodontic pliers 10 generally refers to the distance between the nose end 16 and the handle end 18. This length may be any appropriate length, but is preferably between about 5 inches and about 8 inches. Further, while these first and second arms 12, 14 may be made of any appropriate material, they are preferably made of a material that is substantially non-corrosive, and more preferably a material such as tungsten carbide, titanium, stainless steel, or the like that is both substantially non-corrosive and capable of withstanding repeated exposure to sterilization processes.

Figure 2:
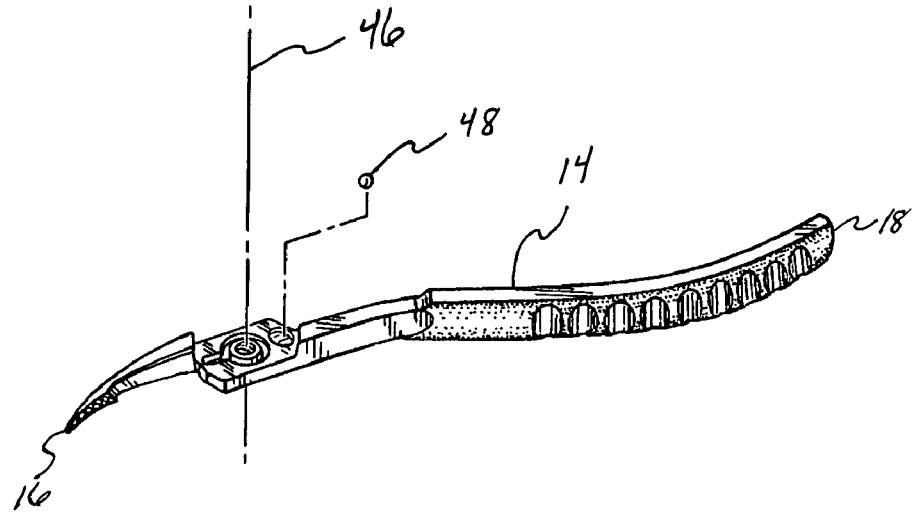
FIG. 2 is an exploded view of the orthodontic pliers of FIG. 1.
Figure 3:
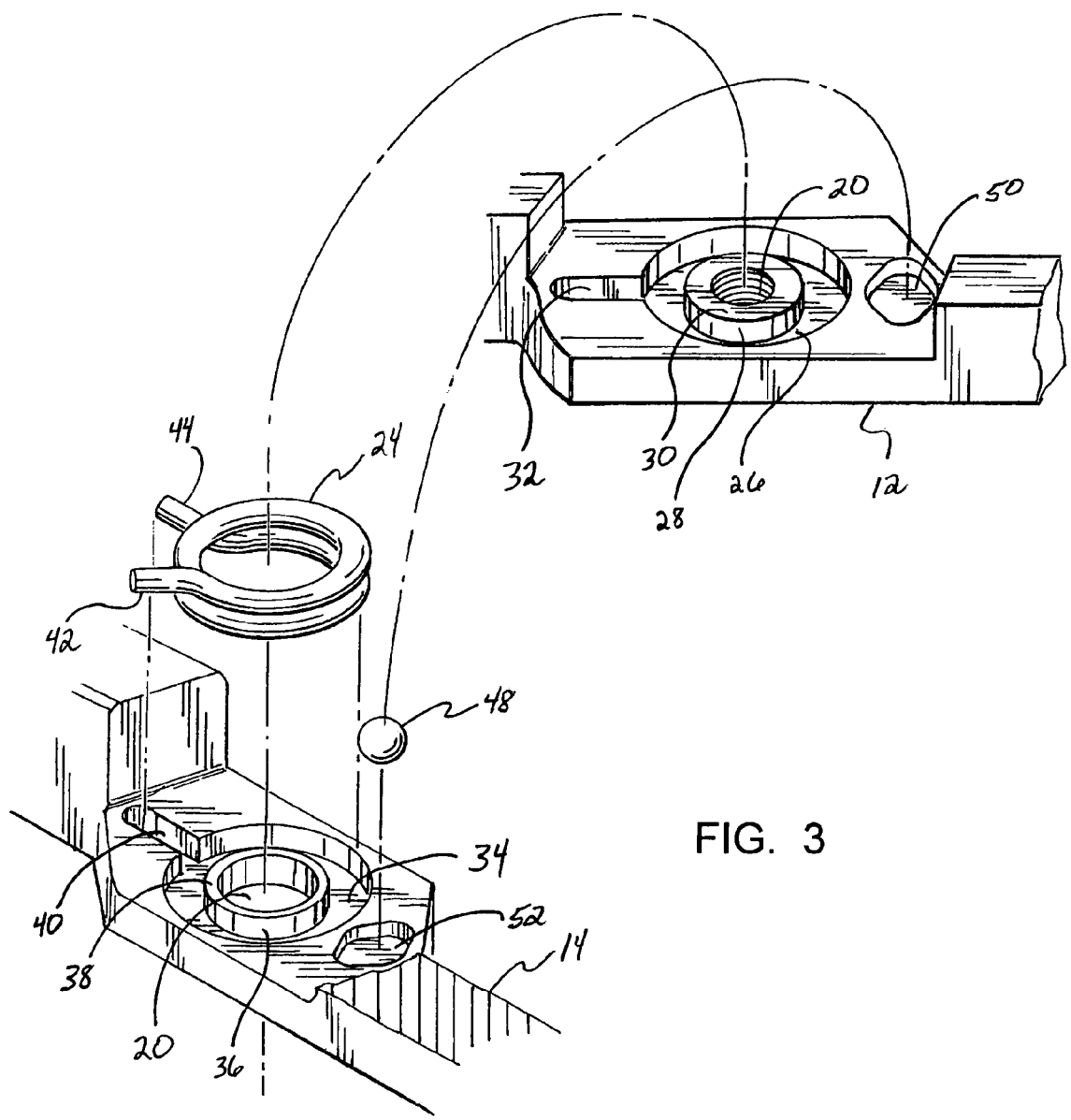
FIG. 3 is a magnified exploded view of the orthodontic pliers of FIG. 1.

As shown in FIGS. 2–3, a fastener aperture 20 is defined in each of the first and second arms 12, 14 to accommodate an appropriate mechanical fastener 22. In the illustrated embodiment, the fastener aperture 20 associated with one of the arms 12, 14 may be threaded, as shown in FIG. 3, to enable the fastener 22 to engage that arm and pivotally interconnect the other arm thereto. In another embodiment, the apertures 20 may be devoid of threading. In such an embodiment, the orthodontic pliers 10 may include a threaded nut that is utilized to threadingly engage a fastener that is disposed through the apertures 20 of the first and second arms 12, 14 to provide a pivotal interconnection of the first and second arms 12, 14. Still other embodiments may utilize other appropriate mechanisms to provide a pivotal interconnection of the first and second arms 12, 14. Incidentally, "pivotally interconnected" or the like means that one component is either directly or indirectly connected (or caused to be connected) with another component in a manner that allows at least one of the components to at least generally undergo a pivoting or pivotal-like motion when exposed to an appropriate force, including without limitation any interconnection that allows a component or a portion thereof to move at least generally about a certain axis.

As shown in FIGS. 2, 3, 5, 6 a spring 24 is disposed generally between the first and second arms 12, 14 and about the mechanical fastener 22. More particularly, and referring to FIG. 3, the first arm 12 has a substantially ring-shaped first recess 26 defined therein. This spring 24 may be made of any appropriate material, but is made of 420 stainless steel in the illustrated embodiment. Further, the wire which makes up the spring 24 may exhibit any of a number of appropriate diameters; however, the wire of the illustrated spring 24 has a diameter of about 1 mm. Still further, the coil of the spring 24 may exhibit any of a number of appropriate inner/outer coil diameters. For instance, the inner diameter of the coil of the spring 24 is about 5 mm, and the outer diameter of the coil of the spring 24 is about 7 mm.

With regard to where the spring 24 is located relative to other portions of the orthodontic pliers 10, an interior wall 28 of the first recess 26 of the first arm is defined by a collar 30 through which the aperture 20 of the first arm 12 is defined. Similarly, the second arm 14 of the orthodontic pliers 10 has a substantially ring-shaped second recess 34 defined therein. An interior wall 36 of this second recess 34 is defined by a collar 38 through which the aperture 20 of the second arm 14 is defined. Since the spring 24 is substantially helical, a portion of the spring 24 can be disposed in or accommodated by the first recess 26 of the first arm 12, and another portion of the spring 24 can be disposed in or accommodated by the second recess 34 of the second arm 14. Accordingly, the collars 30, 38 of the respective arms 12, 14 are generally disposed between the spring 24 and the fastener 22 of the orthodontic pliers 10. While the first and second recesses 26, 34 are illustrated as being substantially ring-shaped, the first and second recesses 26, 34 may exhibit any of a number of other appropriate designs/configurations in other embodiments of the orthodontic pliers 10. Likewise, while the spring 24 is illustrated as being substantially helical or coil-shaped, other spring or spring-type mechanisms may be utilized in other embodiments of the orthodontic pliers 10. It should be noted that the recesses 26, 34 and spring 24 are preferably designed in generally complimentary fashion. In other words, the recesses 26, 34 are preferably configured to accommodate at least a portion of the spring 24.

Still referring to FIG. 3, associated with each of the recesses 26, 34 is a channel. More particularly, the first arm 12 has a first channel 32 defined therein that meets the first recess 26. Likewise, the second arm 14 has a second channel 40 defined therein that meets the second recess 34. These channels 32, 40 are included in the orthodontic pliers 10 to accommodate tangs of the spring 24. Specifically, a first tang 42 of the spring 24 is generally located within the first channel 32 of the first arm 12. Similarly, a second tang 44 of the spring 24 is generally located within the second channel 40 of the second arm 14. While these first and second channels 32, 40 are illustrated as being substantially straight, elongate grooves, the channels of other embodiments of the orthodontic pliers 10 may exhibit any of a number of other appropriate designs/configurations. Likewise, while the tangs 42, 44 of the spring 24 are illustrated as being substantially straight, other embodiments of the orthodontic pliers 10 may include springs with other appropriate tang designs. It should be noted that the channels 32, 40 and the tangs 42, 44 are preferably designed in generally complimentary fashion. In other words, each of the channels 32, 40 of the orthodontic pliers 10 are preferably configured to accommodate the corresponding tang 42, 44 of the spring 24. This design of the spring 24, the recesses 26, 34, and the channels 32, 40 enables the spring 24 to be disposed about pivot axis 46 (FIG. 2) of the orthodontic pliers 10 while effectively preventing significant unitary rotational movement of the entire spring 24 (including the tangs 42, 44) about the pivot axis 46. This arrangement tends to enable the spring 24 to effectively bias the first and second arms 12, 14 of the orthodontic pliers 10 toward an open condition of the orthodontic pliers 10 as shown in FIGS. 4–5.

FIG. 3 illustrates that each of the arms 12, 14 of the orthodontic pliers 10 includes a bearing recess to accommodate a bearing 48. In particular, the first arm 12 has a first bearing recess 50 defined therein, and the second arm 14 has a second bearing recess 52 defined therein. These bearing recesses 50, 52 are designed for each to accommodate at least a portion of the bearing 48. Indeed, it may be said that the first and second bearing recesses 50, 52, in combination, at least generally define a bearing cavity of the orthodontic pliers 10 in which the bearing 48 is housed. It is generally preferred that each of these bearing recesses 50, 52 is substantially four-sided in what may be characterized as a generally quadrilateral or parallelogram shape having rounded corners. However, other embodiments may exhibit other appropriate designs/configurations for these recesses. Incidentally, this bearing 48 may be made of any appropriate bearing material such as, but not limited to, ceramic, stainless steel, titanium, and the like.

Various relational characterizations may be made in relation to the components of the orthodontic pliers 10. For instance, the spring 24 is generally disposed between the bearing 48 and the nose end 16 of the orthodontic pliers 10. Further, the bearing 48 is disposed between the mechanical fastener 22 and the handle end 18 of the orthodontic pliers 10. Still further, the bearing 48 is disposed between the spring 24 and the handle end 18 of the orthodontic pliers 10. While this arrangement is preferred, other embodiments of the orthodontic pliers 10 may exhibit other appropriate arrangements and locations of the spring 24 and the bearing 48.

Figure 4:
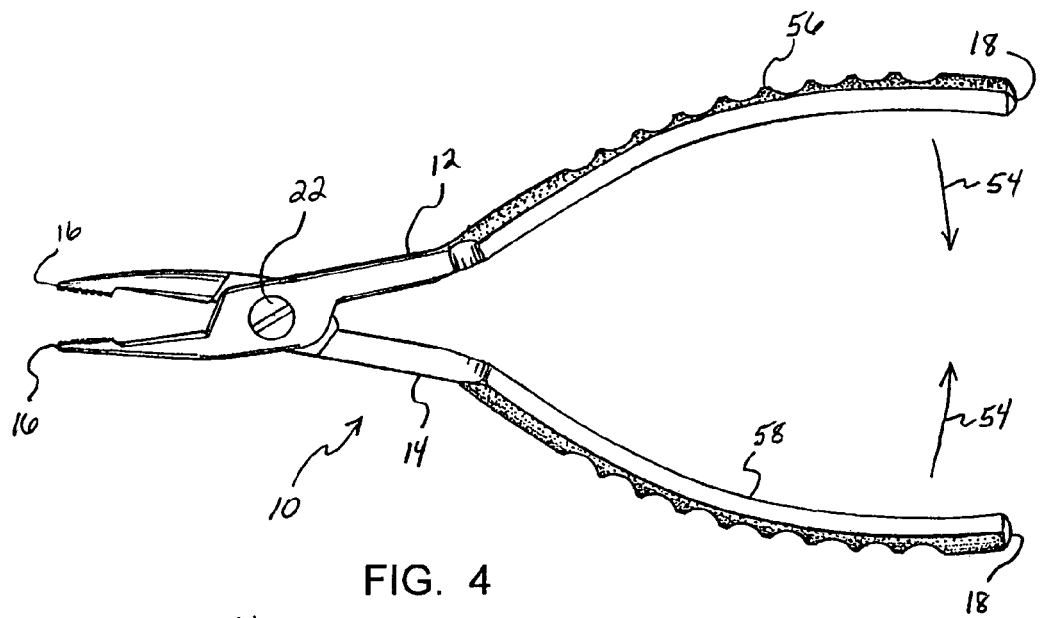
FIG. 4 is a top view of the orthodontic pliers of FIG. 1 in an open condition.
Figure 5:
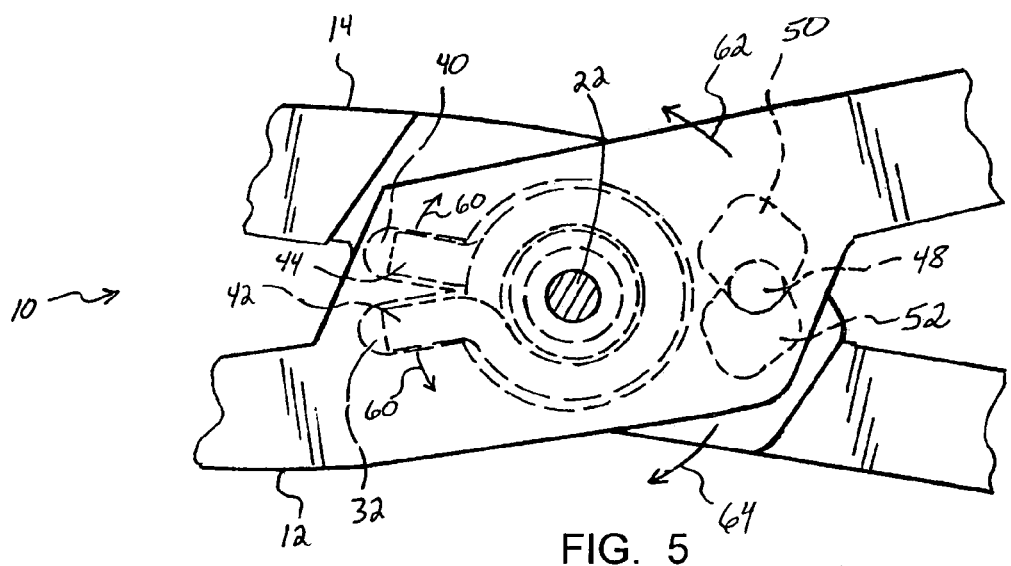
FIG. 5 is a magnified top view of the orthodontic pliers in the open condition of FIG. 4.

As mentioned above, the spring 24 is generally utilized to bias the orthodontic pliers 10 toward an open condition as illustrated in FIGS. 4–5. So, for instance, if no one is urging first and second handle portions 56, 58 of the corresponding first and second arms 12, 14 toward one another in the manner illustrated by arrows 54, the orthodontic pliers 10 are preferably oriented in the open condition. Stated another way, when the orthodontic pliers 10 are not in use, the orthodontic pliers 10 are preferably disposed in or a predisposition for the open position illustrated in FIG. 4.

FIG. 5 illustrates how the spring 24 and bearing 48 relate to the first and second arms 12, 14 when the orthodontic pliers 10 are in the open condition of FIG. 4. In particular, the spring 24 (via the first and second tangs 42, 44) provides a biasing force in the manner indicated by arrows 60 to promote the open condition of FIG. 4. The first and second tangs 42, 44 (as well as the first and second channels 32, 40) are offset (e.g., not aligned) relative to each other when the orthodontic pliers 10 is in this open condition. However, both tangs 42, 44 are generally disposed toward the nose end 16 of the orthodontic pliers 10 and at least generally away from the handle end 18 of the orthodontic pliers 10.

Still referring to FIG. 5, the bearing 48 and the bearing recesses 50, 52 of the respective first and second arms 12, 14 may be said to assist in limiting or generally controlling a range of motion of the orthodontic pliers 10. In particular, the spring 24 tends to bias the arms 12, 14 in a manner that urges the first bearing recess 50 in the direction indicated by arrow 62 and the second bearing recess 52 in the direction indicated by arrow 64. However, the orthodontic pliers 10 may only open to a limited extent because the bearing 48 eventually is "pinched" between the first and second bearing recesses 50, 52 to function as a sort of stop feature of the orthodontic pliers 10. The generally diamond-like shape of the bearing recesses 50, 52 facilitate this stop function. So, when the orthodontic pliers 10 are in the open condition, walls of the first bearing recess 50 are generally offset relative to walls of the second bearing recess 52. In other words, the walls of the first recess 50 are misaligned with the walls of the second recess 52 when the orthodontic pliers 10 is in the open condition. However, the relationship of the bearing 48 with the bearing recesses 50, 52 effectively prevents the bearing recesses 50, 52 from completely dissociating from one another in normal opening and closing operations of the orthodontic pliers 10. That is, the relationship of the bearing 48 with the bearing recesses 50, 52 generally preserves some form of a bearing cavity in which the bearing 48 resides.

Another related benefit of employing the bearing 48 in the orthodontic pliers 10 is that is may be said to generally hinder friction between the first and second arms 12, 14 during movement of the orthodontic pliers 10 between the open and closed positions. While only one bearing is employed in the illustrated embodiment, it is contemplated that other embodiments may include a plurality of bearings to reduce friction between the first and second arms 12, 14.

Figure 6:
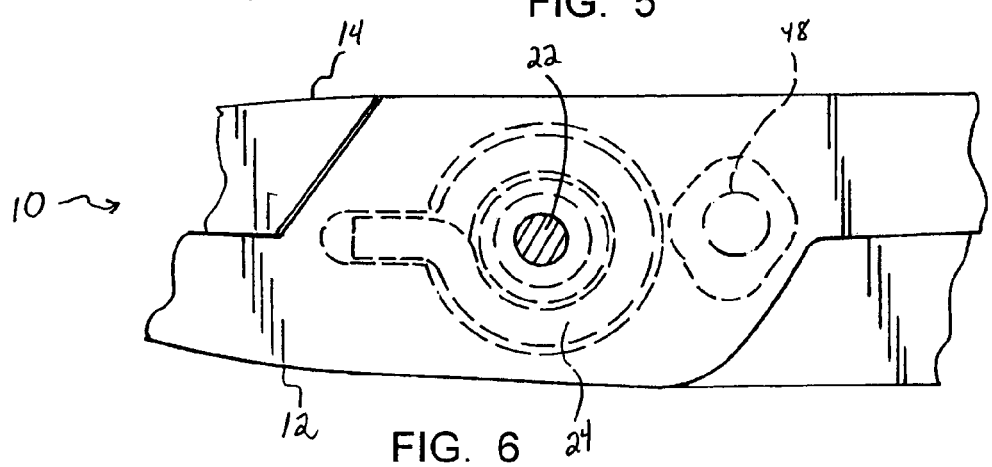
FIG. 6 is a magnified top view of the orthodontic pliers in the closed condition of FIG. 1.

As previously stated, FIGS. 4–5 illustrate the orthodontic pliers 10 in an open condition. This open condition is characterized by the nose end 16 of the first arm 12 being separated from the nose end 16 of the second arm 14. A change in the condition of the orthodontic pliers 10 from the open condition shown in FIGS. 4–5 to the closed position shown in FIGS. 1 and 6 is generally accompanied by several things. Referring to FIG. 4, to close the orthodontic pliers 10, the first and second handle portions 56, 58 of the corresponding arms 12, 14 are generally moved toward each other as indicated by the arrows 54. The spring force imposed on the arms 12, 14 by the spring 24, at least to some degree, inhibits this closing of the orthodontic pliers 10. However, the bearing 48 may be said to facilitate the closing of the orthodontic pliers 10 by hindering friction between the first and second arms 12, 14. When the orthodontic pliers 10 are in the closed condition of FIG. 6, the tangs 42, 44 of the spring 24 overlap or are substantially aligned with one another. Further, the walls of the bearing recesses 50, 52 are also substantially aligned with one another.

Referring to FIG. 1, the orthodontic pliers 10 may be returned (from the closed condition) to the open condition of FIGS. 4–5 by allowing the nose ends 16 of the first and second arms 12 to move away from each other as indicated by arrows 66. Returning the orthodontic pliers 10 to the open condition of FIGS. 4–5 is generally facilitated by the spring force provided to the arms 12, 14 by the spring 24. Further, the hindrance of friction between the arms 12, 14 provided by the bearing 48 also facilitates returning the orthodontic pliers 10 to the open condition. In this regard, it may be said that the orthodontic pliers 10 are generally self-opening.

Incidentally, with regard to the nose end 16 of the orthodontic pliers 10, any of a number of nose designs may be appropriate for the orthodontic pliers 10 of the invention. For instance, the nose design of some embodiments may include a nose design like that of an angle or bird-beak pliers, a lightwire bird-beak pliers, a How pliers, a curved Weingart pliers, a posterior band removing pliers, a bayonet pliers, a lingual arch forming pliers, a light-wire cutting pliers, a distal-end cutting pliers, an omega loop forming pliers, a bracket removal pliers, a Mathieu needle holding pliers, or the like. Further, any of a number of designs for the handle portions 56, 58 may also be appropriate for the orthodontic pliers 10.

Those skilled in the art will now see that certain modifications can be made to the pliers and related methods herein disclosed with respect to the illustrated embodiments, without departing from the spirit of the present invention. And while the invention has been described above with respect to the preferred embodiments, it will be understood that the invention is adapted to numerous rearrangements, modifications, and alterations, and all such arrangements, modifications, and alterations are intended to be within the scope of the appended claims.

What is claimed is:

1. A pliers, comprising:
   a first arm having a first aperture and a first recess defined therein;
   a second arm having a second aperture and a second recess defined therein;
   a mechanical fastener disposed in said first and second apertures and pivotally interconnecting said first and second arms;
   a spring disposed about said mechanical fastener; and
   a bearing disposed between said first and second arms with at least a portion of said bearing being disposed within said first and second recesses; and
   wherein at least one of said first and second recesses is substantially four-sided.

2. A pliers, as claimed in claim 1, wherein:
   said first and second recesses are substantially four-sided.

3. A pliers, as claimed in claim 1, wherein:
   each of said first and second arms comprises a nose end and an opposing handle end, said mechanical fastener is disposed between said nose end and said handle end of each of said first and second arms, and said bearing is disposed between said mechanical fastener and said handle end of each of said first and second arms.

4. A pliers, as claimed in claim 1, wherein:
   each of said first and second arms comprises a nose end and an opposing handle end, said bearing is disposed between said nose end and said handle end of each of said first and second arms, and said spring is disposed between said bearing and said nose end of each of said first and second arms.

5. A pliers, as claimed in claim 1, wherein:
   said first arm has a first recess defined therein disposed about said first aperture, and at least a portion of said spring is disposed in said first recess.

6. A pliers, as claimed in claim 5, wherein:
   said first arm has a first channel defined therein and associated with said first recess, and a first tang of said spring is disposed in said first channel of said first arm.

7. A pliers, as claimed in claim 5, wherein:
   said second arm has a second recess defined therein disposed about said second aperture, and at least a portion of said spring is disposed in said second recess.

8. A pliers, as claimed in claim 7, wherein:
   said first arm has a first channel defined therein and associated with said first recess, and a first tang of said spring is disposed in said first channel of said first arm; and wherein
   said second arm has a second channel defined therein and associated with said second recess, and a second tang of said spring is disposed in said second channel of said second arm.

9. A pliers, as claimed in claim 8, wherein:
   said first and second tangs of said spring are substantially parallel and disposed between said mechanical fastener and said nose end of each of said first and second arms when said pliers is in a closed condition.

10. A pliers, comprising:
    a nose end and an opposing handle end;
    a first and second arms, each defining a portion of said nose end and a portion of said handle end;
    the first arm defining a first recess therein;

the second arm defining a second recess therein
means for pivotally interconnecting said first and second arms;
means for biasing said pliers toward an open condition; and
a bearing disposed between said first and second arms with at least a portion of said bearing being disposed within said first and second recesses; and
wherein at least one of said first and second recesses is substantially four-sided.

11. A pliers, as claimed in claim 10, wherein:
walls of said first recess are substantially aligned with walls of said second recess when said pliers is in a closed condition.

12. A pliers, as claimed in claim 11, wherein:
said walls of said first recess are misaligned with said walls of said second recess when said pliers is in said open condition.

* * * * *